United States Patent
Beelen et al.

(10) Patent No.: US 9,877,989 B2
(45) Date of Patent: Jan. 30, 2018

(54) USE OF PREPARATIONS COMPRISING EXOSOMES DERIVED FROM MESENCHYMAL STEM CELLS (MSCS) IN THE PREVENTION AND THERAPY OF INFLAMMATORY CONDITIONS

(71) Applicant: Universitaet Duisburg-Essen, Essen (DE)

(72) Inventors: Dietrich Wilhelm Beelen, Essen (DE); Thorsten Doeppner, Essen (DE); Ursula Felderhoff-Mueser, Essen (DE); Bernd Giebel, Essen (DE); Dirk Hermann, Essen (DE); Peter Horn, Essen (DE); Matthias Keller, Haibach (AT); Lambros Kordelas, Duesseldorf (DE); Anna-Kristin Ludwig, Essen (DE); Vera Rebmann, Essen (DE)

(73) Assignee: UNIVERSITAET DUISBURG-ESSEN, Essen (DE)

( * ) Notice: Subject to any disclaimer, the term of this patent is extended or adjusted under 35 U.S.C. 154(b) by 0 days.

(21) Appl. No.: 14/414,843

(22) PCT Filed: Jul. 18, 2013

(86) PCT No.: PCT/EP2013/065219
§ 371 (c)(1),
(2) Date: Jan. 14, 2015

(87) PCT Pub. No.: WO2014/013029
PCT Pub. Date: Jan. 23, 2014

(65) Prior Publication Data
US 2015/0190429 A1 Jul. 9, 2015

(30) Foreign Application Priority Data

Jul. 18, 2012 (EP) .................................... 12176968

(51) Int. Cl.
| | |
|---|---|
| C12N 5/02 | (2006.01) |
| A61K 35/28 | (2015.01) |
| A61K 38/17 | (2006.01) |
| A61K 9/00 | (2006.01) |
| A61K 38/18 | (2006.01) |
| A61K 38/19 | (2006.01) |
| A61K 38/20 | (2006.01) |
| A61K 38/21 | (2006.01) |

(52) U.S. Cl.
CPC ............ *A61K 35/28* (2013.01); *A61K 9/0019* (2013.01); *A61K 38/17* (2013.01); *A61K 38/1709* (2013.01); *A61K 38/1841* (2013.01); *A61K 38/19* (2013.01); *A61K 38/2053* (2013.01); *A61K 38/2066* (2013.01); *A61K 38/217* (2013.01)

(58) Field of Classification Search
None
See application file for complete search history.

(56) References Cited

U.S. PATENT DOCUMENTS

| 6,812,023 B1 * | 11/2004 | Lamparski | C12N 5/0639 435/325 |
|---|---|---|---|
| 8,932,855 B2 * | 1/2015 | Gabrielsson | A61K 39/00 435/372.2 |
| 2013/0143314 A1 * | 6/2013 | Shiels | A61K 35/22 435/320.1 |
| 2013/0195899 A1 * | 8/2013 | Ichim | A61K 35/12 424/184.1 |
| 2013/0209528 A1 * | 8/2013 | Levi | A61K 35/28 424/400 |

FOREIGN PATENT DOCUMENTS

| WO | WO 2006/007529 | * | 1/2006 |
|---|---|---|---|
| WO | WO 2009/105044 | * | 8/2009 |
| WO | WO 2011/000551 | * | 1/2011 |
| WO | WO 2012/020307 A2 | | 2/2012 |
| WO | WO 2012/053976 A1 | | 4/2012 |
| WO | WO 2012/087241 A1 | | 6/2012 |

OTHER PUBLICATIONS

Mixed lymphocyte reaction From Wikipedia, the free encyclopedia downloaded pp. 1-2; Oct. 7, 2016.*
Baron, Frédéric et al., "Mesenchymal Stromal Cells: A New Tool Against Graft-Versus-Host Disease?", *Biol. Blood Marrow Transplant*, 2012, 18(6):822-40.
Lai, Ruenn Chai et al., "Exosome secreted by MSC reduces myocardial ischemia/reperfusion injury," *Stem Cell Research*, 2010, 4:214-222.
Lee, Ryang Hwa et al., "Intravenous hMSCs Improve Myocardial Infarction in Mice because Cells Embolized in Lung Are Activated to Secrete the Anti-inflammatory Protein TSG-6," *Cell Stem Cell*, 2009, 5(1):54-63.
Schütt, Philipp et al., "Prognostic relevance of soluble human leukocyte antigen—G and total human leukocyte antigen class I molecules in lung cancer patients," *Human Immunol.*, 2010, 71(5):489-495.

* cited by examiner

*Primary Examiner* — Maria Leavitt
(74) *Attorney, Agent, or Firm* — Saliwanchik, Lloyd & Eisenschenk

(57) ABSTRACT

The present invention relates to the use of exosome-preparations derived from neonatal or adult tissue-derived mesenchymal stem-cells (MSCs) for the prevention or for therapy of inflammatory conditions, such as, for example, pre- and postnatally acquired damages of the brain (i.e. neuronal damages) or in complications following stem cell transplantation ("graft vs host-disease", GvHD).

2 Claims, 10 Drawing Sheets

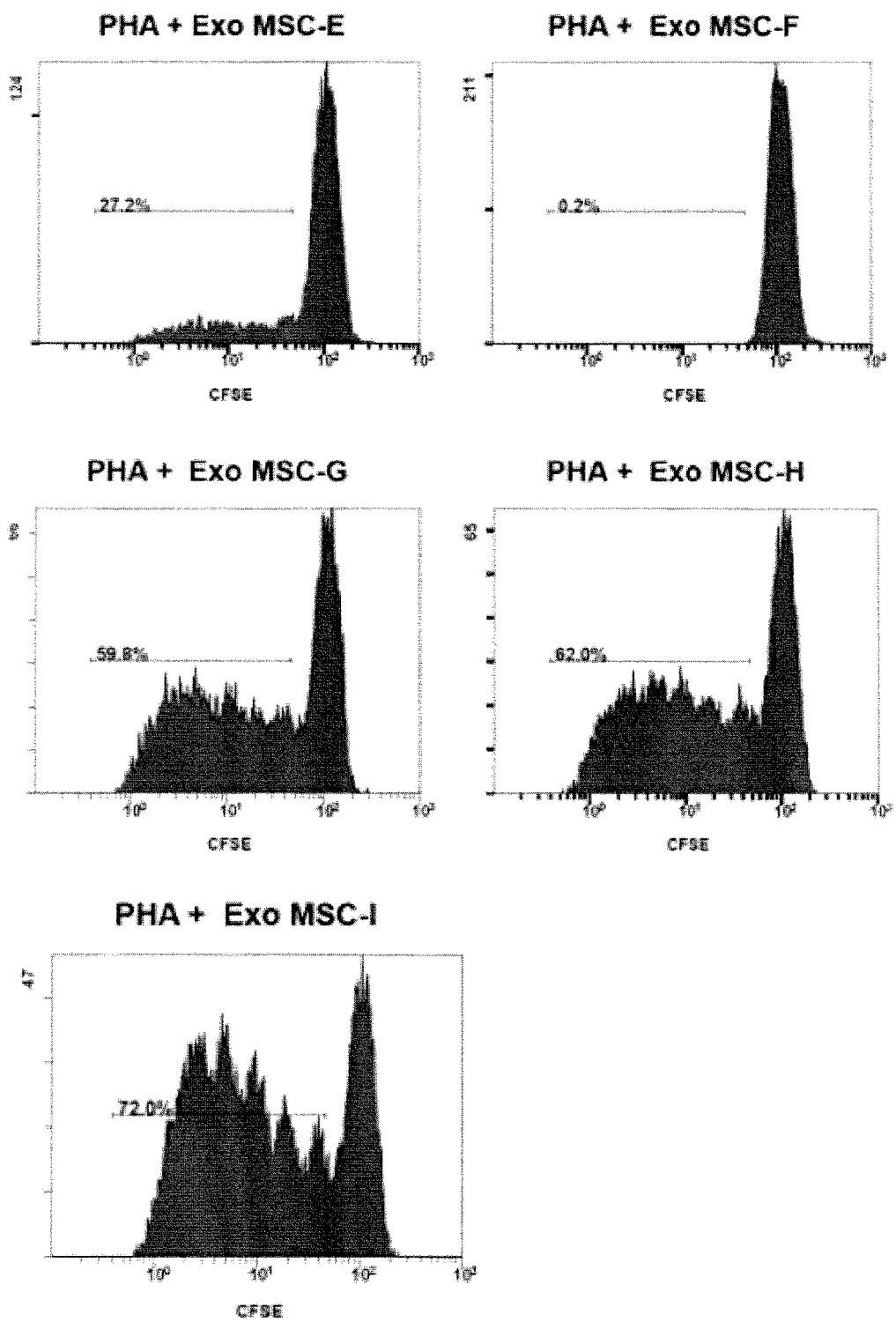
Figure 6: continued

A)

B)

USE OF PREPARATIONS COMPRISING EXOSOMES DERIVED FROM MESENCHYMAL STEM CELLS (MSCS) IN THE PREVENTION AND THERAPY OF INFLAMMATORY CONDITIONS

CROSS REFERENCE TO RELATED APPLICATIONS

This application is a National Stage Application of International Application Number PCT/EP2013/065219, filed Jul. 18, 2013; which claims priority to German Application No. 12176968.1, filed Jul. 18, 2012; all of which are incorporated herein by reference in their entirety.

The present invention relates to the use of exosome-preparations derived from neonatal or adult tissue-derived mesenchymal stem-cells (MSCs) for the prevention or for therapy of inflammatory conditions, such as, for example, pre- and postnatally acquired damages of the brain (i.e. neuronal damages) or in complications following stem cell transplantation ("graft vs host-disease", GvHD).

BACKGROUND OF THE INVENTION

Different cell populations appear as candidates for cell-based therapies, in particular in neonates: Hematopoietic stem cells (HSC), endothelial progenitor cells (EPC), mesenchymal stem cells (MSC) as well as regulatory T cells (Treg) exerting immune modulatory and pro-regenerative activities by direct cellular action or secretion of pro-regenerative, anti-apoptotic, immunomodulatory factors. The suppressive activity of Tregs from umbilical cord blood (UCB) has been attributed to the observed reduced severity of graft versus host disease (GvHD) in UCB transplantation (Tolar J, Hippen K L, Blazar B R. Immune regulatory cells in umbilical cord blood: T regulatory cells and mesenchymal stromal cells. Br J Haematol 2009 October; 147(2):200-6).

Mesenchymal stem/stromal cells (MSCs) have emerged as one of the most intensely studied adult stem cell population within the last 15 years (Bieback K, Brinkmann I. Mesenchymal stromal cells from human perinatal tissues: From biology to cell therapy. World J Stem Cells 2010 Aug. 26; 2(4):81-92). The therapeutic interest initially was based on their multi-lineage differentiation potential. However, it recently turned out that only few cells engraft and differentiate after either local or systemic delivery of MSCs in a number of different injury models. Subsequent to the detection of profound immune modulatory activities, MSCs were successfully applied to treat steroid-refractory GvHD (Le Blanc K, Rasmusson I, Sundberg B, Gotherstrom C, Hassan M, Uzunel M et al. Treatment of severe acute graft-versus-host disease with third party haploidentical mesenchymal stem cells. Lancet 2004 May 1; 363(9419):1439-41).

Since then, a number of different studies have addressed the impact of MSCs on GvHD with different outcomes. In most of these studies, the infusion of MSCs appeared to be safe. However, a positive impact on GvHD is still discussed controversially (Baron and Storb, 2011). Although MSCs can be raised from virtually every tissue within the human body, they are a very rare population comprising about 0.001 to 5% of cells in different tissues (Bieback K. Basic Biology of Mesenchymal Stem Cells. Transfus Med Hemother 2008; 35(3):151-2).

Exosomes are naturally occurring small membrane vesicles (80-160 nm) released by a huge variety of cell species. Containing a combination of lipids and proteins as well as RNAs, exosomes participate in intercellular communication processes. They can be isolated from all body fluids including blood plasma, urine, saliva, breast milk, bronchial lavage fluid, cerebral spinal fluid, amniotic fluid and malignant ascites (Ludwig A K, Giebel B. Exosomes: Small vesicles participating in intercellular communication. Int J Biochem Cell Biol 2011 Oct. 19).

Initially, exosomes were discovered in 1983 as small vesicles that are released by exocytosis upon fusion of so called multivesicular bodies with the plasma membrane. In 1996, exosomes were isolated from B lymphocytes, and were demonstrated to exhibit antigen-presenting characteristics. Since then, their role in immune-biological settings has been investigated in an increasing number of studies. It turned out that exosomes derived from mature dendritic cells for example exert immune-stimulatory functions, while tumor-derived exosomes often mediate immune-suppressive functions (Ludwig A K, Giebel B. Exosomes: Small vesicles participating in intercellular communication. Int J Biochem Cell Biol 2011 Oct. 19).

In 2010, Lai and co-workers provided evidence that exosomes released from MSCs mediate at least a proportion of the regenerative effects of clinically applied MSCs (Lai R C, Arslan F, Lee M M, Sze N S, Choo A, Chen T S et al. Exosome secreted by MSC reduces myocardial ischemia/reperfusion injury. Stem Cell Res 2010 May; 4(3):214-22). Since intravenously administered MSCs get rapidly trapped into the lung and are hardly found within infarcted hearts (Lee et al., 2009), the group of Lim searched for paracrine MSC effectors and showed in a first set of experiments that the supernatants of in vitro expanded MSCs are sufficient to mediate beneficial effects. Next, they purified exosomes from MSC supernatants and infused them in a murine myocardial ischemia model. Again, they observed a reduction of the infarct size (Lai et al., 2010).

Timmers et al. (in Timmers L, Lim S K, Arslan F, Armstrong J S, Hoefer I E, Doevendans P A, Piek J J, El Oakley R M, Choo A, Lee C N, Pasterkamp G, de Kleijn D P. Reduction of myocardial infarct size by human mesenchymal stem cell conditioned medium. Stem Cell Res. 2007 November; 1(2):129-37. Epub 2008 Mar. 8) describe the use of secretions of human MSCs as a therapeutic option in acute myocardial infarct. These MSCs are raised from human Embryonic Stem Cells (hESCs).

Fleissner et al. (in: Fleissner F, Goerzig Y, Haverich A, Thum T. Microvesicles as novel biomarkers and therapeutic targets in transplantation medicine. Am J Transplant. 2012 February; 12(2):289-97. Epub 2011 Nov. 14) describe microvesicles (MVs) including exosomes as emerging new biomarkers and potential regulators of inflammation and immunological processes. The particles contain proteins and genetic information including DNA and microRNAs that may be of importance for cell/cell communication. However, their role during and after organ transplantation and immunomodulatory effects is described to be only in its beginning of understanding. The authors speculate that MV modulation may emerge as a therapeutic approach in organ rejection therapy.

Horstman et al. (in: Horstman L L, Jy W, Minagar A, Bidot C J, Jimenez J J, Alexander J S, Ahn Y S. Cell-derived microparticles (MPs) and exosomes in neuroinflammatory disorders. Int Rev Neurobiol. 2007; 79:227-68) describe MPs and their possible roles in the pathophsyiology of some neuropathologies, especially those which are ischemic in nature, but probably also inflammatory ones. Tables include a listing of bioactive agents known to be carried on MP, many of which were heretofore considered strictly soluble, and some of which can be transferred from cell to cell via MP vectors, for example certain cytokine receptors.

Baron and Storb (in: Baron F, Storb R. Mensenchymal Stromal Cells: A New Tool against Graft-versus-Host Disease? Biol Blood Marrow Transplant 2011 Sep. 29) propose that immune modulatory activities of MSCs are thought to derive from secreted soluble factors rather than from direct intercellular interactions of engrafted MSCs with the patient's immune cells.

WO 2009/105044 describes a particle secreted by a mesenchymal stem cell and comprising at least one biological property of a mesenchymal stem cell. The biological property may comprise a biological activity of a mesenchymal stem cell conditioned medium (MSC-CM) such as cardioprotection or reduction of infarct size. The particle may comprise a vesicle or an exosome. The claims encompass exosomes obtainable from human embryonic stem cells derived from human embryos.

WO 2012/020308 is directed at compositions and methods for the treatment of tissue damage (e.g., acute or chronic) and related diseases, disorders or conditions based on the use of pathfinder cells, extracellular secretomes thereof, and/or pathfinder cell-associated micro RNAs (miR-NAs). In some embodiments, the present invention provides a method for treating inflammation comprising a step of administering a population of cells, or extracellular secretomes thereof, to an individual suffering from a disease, disorder or condition characterized by inflammation of one or more tissues, wherein the cells are originated from an adult tissue and wherein the cells induce an anti-inflammatory response.

WO 2012/053976 discloses the use of exosomes that are secreted by mesenchymal stem cells in order to promote hair growth and wound healing. These effects are disclosed in connection with pro-inflammatory cytokines and proteases. WO 2012/053976 speculates about an immune-modulatory effect of the exosome-preparation.

WO 2012/020307 discloses the therapeutic use of microvesicles including exosomes in the treatment of inflammation and lesions of cerebral trauma. Similarly, WO 2012/087241 describes the use of exosomes for the treatment of the diseases as mentioned.

The currently proposed strategies in the prevention and/or therapy based on exosomes suffer from several disadvantages. Most problematic is their unimodal approach. This is in contrast to the biological complexity of the pathophysiology of the indications to be treated. Instead, it would be required to use a therapeutic cocktail that can interact with very different pathophysiological signaling cascades, and thus provide a more complete and effective prevention or treatment.

Mesenchymal stromal cells (MSCs) represent a heterogeneous subset of multipotent cells that can be isolated from several tissues including bone marrow and fat. MSCs exhibit immunomodulatory and anti-inflammatory properties that prompted their clinical use as prevention and/or treatment for severe graft-versus-host disease (GvHD). Although a number of phase III studies have suggested that MSC infusion was safe and might be effective for preventing or treating acute GvHD, definitive proof of their efficacy remains lacking thus far. Multicenter randomized studies are ongoing to more precisely assess the impact of MSC infusion on GvHD prevention/treatment, whereas further research is performed in vitro and in animal models with the aims of determining the best way to expand MSCs ex vivo as well as the most efficient dose and schedule of MSCs administration (see Baron and Storb, 2011). Although MSCs can be raised from virtually every tissue within the human body, they are a very rare population comprising about 0.001 to 5% of cells in different tissues. Especially UCB contains MSC at low frequency. Also, MSCs derived from human embryonic ESC meet ethical concerns.

Finally, exosomes that are obtained from MSCs of individual donors were found to be very heterogenic. Thus, it seems reasonable to assume that subtypes of populations of MSCs with quite different potential are present. Currently, this problem is completely unresolved.

It is therefore an object of the present invention to provide a safe and more effective preparation of exosomes that is suitable for the treatment of diseases and conditions that involve inflammatory reactions. Other objects of the present invention will become apparent to the person of skill upon studying the present description of the invention.

In a first aspect thereof, the above object is solved by a pharmaceutical preparation comprising exosomes, obtainable by a method comprising the following steps:
a) providing a cell culture medium supernatant from neonatal or adult tissue-derived mesenchymal stem-cells (MSCs) comprising exosomes,
b) enriching said exosomes, optionally comprising polyethylene glycol precipitation,
c) determining an in vitro immunomodulatory effect, in particular an anti-inflammatory effect and/or immune suppressive effect, of said enriched exosomes by, for example, a reduced IL-1β, TNF-α, T-cell proliferation, and/or IFN-γ cytokine response of effector cells of a donor, and
d) selecting those enriched exosomes that exhibit an immunomodulatory effect, in particular an anti-inflammatory effect and/or immune suppressive effect.

Considering exosomes as a novel, very potent tool in regenerative and in immune-modulatory therapies, the inventors have set up new purification strategies and technologies to enrich for and to analyze exosomes. Amongst other indications, the inventors evaluated their applicability for use in immune-modulatory (inflammatory) therapies, such as GvHD therapy, and already treated an otherwise treatment-resistant grade IV acute GvHD patient with MSC-derived exosomes. The GvHD symptoms of the patient decreased dramatically with the specific exosome therapy and the patient remained stable for five months.

Furthermore, in order to prove effectiveness of the prevention and therapy of neuronal damages, in particular in neonates, experiments with LPS confronted rats were performed that showed a clear positive reaction following the administration of the inventive pharmaceutical preparation.

Preferred is a pharmaceutical preparation according to the present invention, wherein said neonatal or adult tissue-derived mesenchymal stem-cells (MSCs) comprising exosomes are selected from human MSCs, and preferably from human MSCs derived from umbilical cord blood, umbilical cord tissue, placenta, bone or adipose tissue. The stem cells of the present invention are strictly non-embryonic derived stem cells. Most preferably, the MSCs that have been cultured in the presence of platelet lysate, and the preparation can contain said lysate and/or fractions thereof.

The pharmaceutical preparation according to the present invention is specifically enriched for exosomes. For this, generally any suitable method for purifying and/or enriching can be used, such as methods comprising magnetic particles, filtration, dialysis, ultracentrifugation, ExoQuick™ (Systems Biosciences, CA, USA), and/or chromatography. Nevertheless, preferred is a method that comprises polyethylene glycol precipitation and/or chromatographically enrichment using the monolithic technology (e.g. CIM®, BIA separations, Austria) as stationary phases instead of columns packed with porous particles. Monoliths are continuous stationary phases that are cast as a homogeneous column in a single piece and prepared in various dimensions with agglomeration-type or fibrous microstructures. (see Iberer, G., Hahn, R., Jungbauer, A. LC-GC, 1999, 17, 998). Using these methods, surprisingly active fractions containing exosomes could be obtained.

Then, in order to identify the most suitable fraction according to the invention fractions being enriched with exosomes are tested for their in vitro immunomodulatory effect, in particular an anti-inflammatory effect and/or immune suppressive effect, and can further be analyzed, in microbiological, in virulence and in pyrogen tests to, for example, excluded possible contaminations. In addition, these fractions can be studied with regard to protein content, and particle size.

It could be found that fractions being enriched with exosomes were particularly useful in the methods according to the present invention, if they exhibited strong in vitro immunomodulatory effects in activity tests, where, following the addition of said exosome fraction, a reduced IL-1β, TNF-α and/or IFN-γ cytokine response of effector cells of a donor could be found. ELISpot assays showed that the IL-1β, TNF-α and/or IFN-γ cytokine response of effector cells are impaired towards allogeneic cells in the presence of exosome containing fractions. Other methods that could be used to test for in vitro immunomodulatory effects include, for example, Luminex, ELISA, and/or flow cytometry.

The present invention is thus based on the novel concept for an improved prevention and treatment of diseases, in particular in patients suffering from a having a risk of an inflammatory disease, neuronal disease, GvHD, stroke, and ischemia and associated complications, for example, for avoiding inflammatory reactions prior or during surgery, and the prevention of inflammatory conditions and reactions of patients that are connected to a life support machine. In one embodiment, the diseases can be selected from pre- or postnatal damages of the nervous system, such as for example, brain damages related to hypoxia, inflammation, and/or ischemia. In another embodiment, the diseases can be selected from graft-versus-host disease, or transplant rejections following organ transplantations, respectively.

In a particularly preferred embodiment of the invention, the exosomes-enriched fractions derived from adult mesenchymal stem cells (MSCs) that were enriched using a polyethylene glycol precipitation protocol, are prophylactically and/or therapeutically transfused into patients, in particular neonates and/or patients receiving transplants and/or patients undergoing surgery.

Preferably, the exosomes-enriched fractions are derived from MSCs that are selected from human adult MSCs, and preferably from human MSCs derived from umbilical cord blood, umbilical cord tissue, placenta, bone or adipose tissue, and MSCs that have been cultured in platelet lysate.

The pharmaceutical preparation according to the present invention preferably is enriched for exosomes that comprise biological factors, such as, for example, proteins, such as anti-inflammatory cytokines, IL-10, TGF-β1, and HLA-G, and/or nucleic acids, such as, for example, miRNAs. This leads to the further advantage according to the invention that a) a multimodal (complex) intervention is performed, b) biological physiological ("self") substances are used, and c) unwanted side effects of the preparation are reduced.

The present invention constitutes a multimodal intervention, and thus not only a specific factor is used (and only a part of the cascade (or of the underlying clinical phenotype) would be intervened with), but biologically complex and endogenous mediators and modulators are used. These components are found in every human, and therefore no significant adverse side-effects are expected.

Preferred is a pharmaceutical preparation according to the present invention, wherein said levels of TGF-β1 as measured in the activity tests are at least ten times higher (at $60.5 \times 10^8$ particles/mL) in the preparation, preferably at least 20 times higher, than in plasma levels of healthy controls. Further preferred is a pharmaceutical preparation according to the present invention, wherein the numbers of IL-1β, TNF-α and/or IFN-γ producing PBMC were found to be reduced in said patient more than fifty percent after the last application (p<0.0001, One-way ANOVA), compared to the cytokines' responses before MSC-exosome administration.

Further preferred is a pharmaceutical preparation according to the present invention, wherein said exosomes have a size of between about 70 to 200 nm, preferably between about 70 to 140 nm, or more preferably between about 70 to 120 nm. "About" shall mean a +/−10% deviation. Further preferred, the exosomes are positive for cellular exosome markers, and even further preferred the protein content of the pharmaceutical preparation is higher than 1 mg/ml.

In another aspect of the present invention, the pharmaceutical preparation according to the present invention, is suitable for i.v. administration, such as for example, intravenous administration or infusion into a patient in need thereof.

Another aspect of the present invention then relates to a method for producing a pharmaceutical preparation according to the present invention, comprising the following steps: a) providing a cell culture medium supernatant from neonatal or adult tissue-derived mesenchymal stem-cells (MSCs), optionally from MSCs that have been cultured in platelet lysate, comprising exosomes, b) enriching said exosomes, optionally comprising polyethylene glycol precipitation, c) determining an in vitro immunomodulatory effect, in particular an anti-inflammatory effect and/or immune suppressive effect, of said enriched exosomes by, for example, a reduced IL-1β, TNF-α, T-cell proliferation, and/or IFN-γ cytokine response of effector cells of a donor, d) selecting those enriched exosomes that exhibit an immunomodulatory effect, in particular an anti-inflammatory effect and/or immune suppressive effect, and e) admixing said enriched exosomes of step d) with at least one suitable pharmaceutical excipient and/or carrier.

Preferred is a method for producing a pharmaceutical preparation according to the present invention, wherein said neonatal or adult tissue-derived mesenchymal stem-cells (MSCs) comprising exosomes are selected from human MSCs, and preferably from human MSCs derived from umbilical cord blood, umbilical cord tissue, placenta, bone or adipose tissue. The stem cells of the present invention are strictly non-embryonic derived stem cells. Most preferably, the MSCs that have been cultured in the presence of platelet lysate, and the preparation can contain said lysate and/or fractions thereof.

The method for producing a pharmaceutical preparation according to the present invention comprises the step of specifically enriching for exosomes. For this, generally any suitable method for purifying and/or enriching can be used, such as methods comprising magnetic particles, filtration, dialysis, ultracentrifugation, ExoQuick™ (Systems Biosciences, CA, USA), and/or chromatography. Nevertheless, preferred is a method that comprises polyethylene glycol precipitation and/or a monolithic method (see above), since using these methods, surprisingly active fractions containing exosomes could be obtained.

Preferred is a method for producing a pharmaceutical preparation according to the present invention, wherein fractions that were enriched for exosomes are further analyzed in microbiological tests, virulence tests, protein content, pyrogen tests, and particle size, in order to identify the most suitable fraction according to the invention.

It could be found that fractions that were enriched for exosomes were particularly useful in the methods according to the present invention, if they exhibited strong in vitro immunomodulatory effects in activity tests, where upon the addition of said exosome fraction, a reduced IL-1β, TNF-α and/or IFN-γ cytokine response of effector cells of a donor could be found. Preferred is a method according to the present invention, wherein said levels of TGF-β1 as measured in the activity tests are at least ten (or at least twenty) times higher (at $60.5 \times 10^8$ particles/mL) in the preparation than in plasma levels of healthy controls. Further preferred is a method according to the present invention, wherein said exosomes have a size of between about 70 to 200 nm, preferably between about 70 to 140 nm, or more preferably between about 70 to 120 nm. "About" shall mean a+/−10% deviation. Further preferred, the exosomes are positive for cellular exosome markers, and even further preferred the protein content of the pharmaceutical preparation is higher than 1 mg/ml.

Furthermore, the method for producing a pharmaceutical preparation according to the present invention comprises d) admixing said enriched exosomes of step c) with at least one suitable pharmaceutical excipient and/or carrier. In general any suitable pharmaceutically acceptable excipient and/or carrier can be used. Preferably, said pharmaceutically acceptable excipient and/or carrier renders said preparation suitable for i.v. administration, such as for example, intravenous administration or infusion.

Yet another aspect of the present invention then relates to a pharmaceutical preparation comprising exosomes derived from a cell culture medium supernatant from neonatal or adult tissue-derived mesenchymal stem-cells (MSCs), preferably according to the present invention as described herein for use in the prevention and/or treatment of diseases.

Preferably, the diseases that are prevented and/or treated using the pharmaceutical preparation comprising exosomes derived from a cell culture medium supernatant from neonatal or adult tissue-derived mesenchymal stem-cells (MSCs) according to the present invention are selected from the group consisting of inflammatory diseases, neuronal diseases, transplant rejections, GvHD, stroke, and ischemia.

Preferably, the diseases that are prevented and/or treated using the pharmaceutical preparation comprising exosomes derived from a cell culture medium supernatant from neonatal or adult tissue-derived mesenchymal stem-cells (MSCs) according to the present invention are selected from pre- or postnatal damages of the nervous system, such as for example, brain damages related to hypoxia, inflammation, and/or ischemia.

Most preferably, the diseases that are prevented and/or treated using the pharmaceutical preparation comprising exosomes derived from a cell culture medium supernatant from neonatal or adult tissue-derived mesenchymal stem-cells (MSCs) according to the present invention are selected from graft-versus-host disease, and transplant rejections following organ or bone marrow transplantation.

Yet another aspect of the present invention according to the present invention then relates to a method for preventing and/or the treatment of a disease selected from the group consisting of inflammatory diseases, neuronal diseases, transplant rejections, stroke, and ischemia in a patient, comprising administering to said patient an effective amount of a pharmaceutical preparation according to the present invention. Preferably, the disease that is prevented and/or treated is selected from pre- or postnatal damages of the nervous system, such as for example, brain damages related to hypoxia, inflammation, ischemia, graft-versus-host disease, and transplant rejections following organ transplantation.

Preferably, said preventing and/or the treatment according to the present invention comprises an administration through i.v. administration, such as for example, intravenous administration or infusion.

More preferred is a method for preventing and/or the treatment of a disease according to the present invention, wherein said patient is a newborn.

The invention thus also relates to the application of exosome-enriched fractions for the treatment of acquired neonatal as well as adult neural defects, for example the treatment of brain damages in neonates and grown-ups after hypoxia, inflammation, ischemia, etc. Furthermore, the treatment of ischemic strokes can be treated, and the adverse effect of the stroke can be reduced and/or reversed.

The invention thus also relates to the application of exosome-enriched fractions for the treatment of transplantation-related complications. Here, primarily the treatment of GvHD, and the rejection of solid organs following transplantation have to be named. Treatments can be both prophylactic and/or therapeutic.

Based on their proposed broad multi-lineage differentiation potential mesenchymal stem cells (MSCs) became one of the most intensively studied adult stem cell entities within the last 15 years. Up to now, more than 300 different NIH-registered studies have addressed potential therapeutic impacts of clinically administered MSCs in a variety of clinical settings including treatment of acute myocardial infarction, stroke and acute kidney failure.

Several studies showed that the vast majority of intravenously administered MSCs get rapidly trapped in the lung and are rarely recovered in other tissues. Therefore, MSCs might improve clinical outcomes by paracrine effects rather than by their previously proposed engraftment into damaged host tissues (Lee et al., 2009). Indeed, the group of Lim earlier showed that the supernatants of in vitro expanded embryonic stem cell derived MSCs contain small extracellular vesicles, so called exosomes, whose infusion is sufficient to mediate a reduction of myocardial infarction sizes (see Lim et al., 2010).

The present invention will now be described further in the following examples, nevertheless, without being limited thereto. For the purpose of the present invention, all references as cited are incorporated by reference in their entireties.

Figure 3:
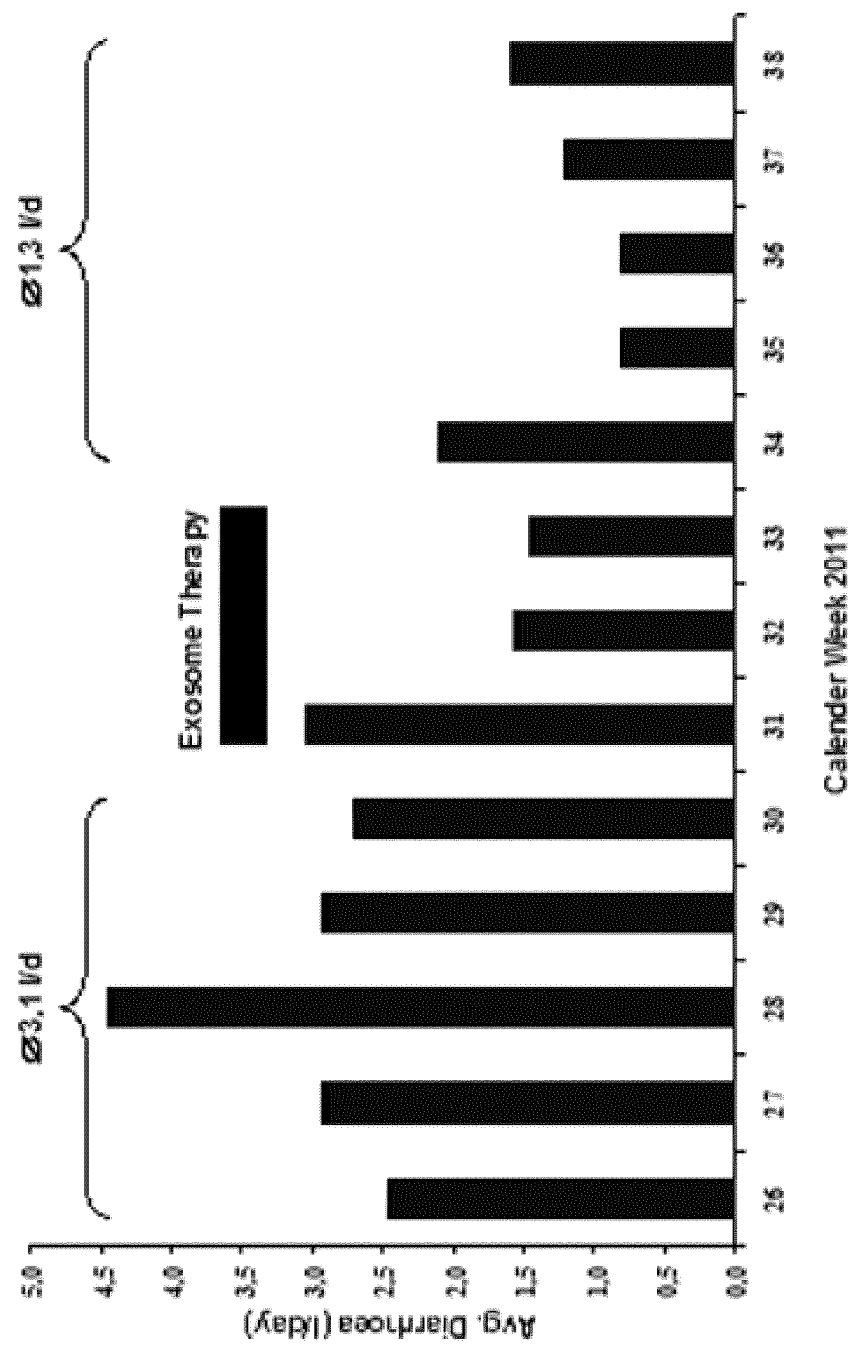

FIG. 3 shows the transplantation-relevant effects of exosomes on a patient in a treatment scheme according to the examples. As symptom of GvHD the patient has diarrhea of more than 3 liters per day. After administration of MSC-derived exosome-enriched fractions, the symptoms were drastically reduced, without that other side-effects could be observed.

Figure 4:
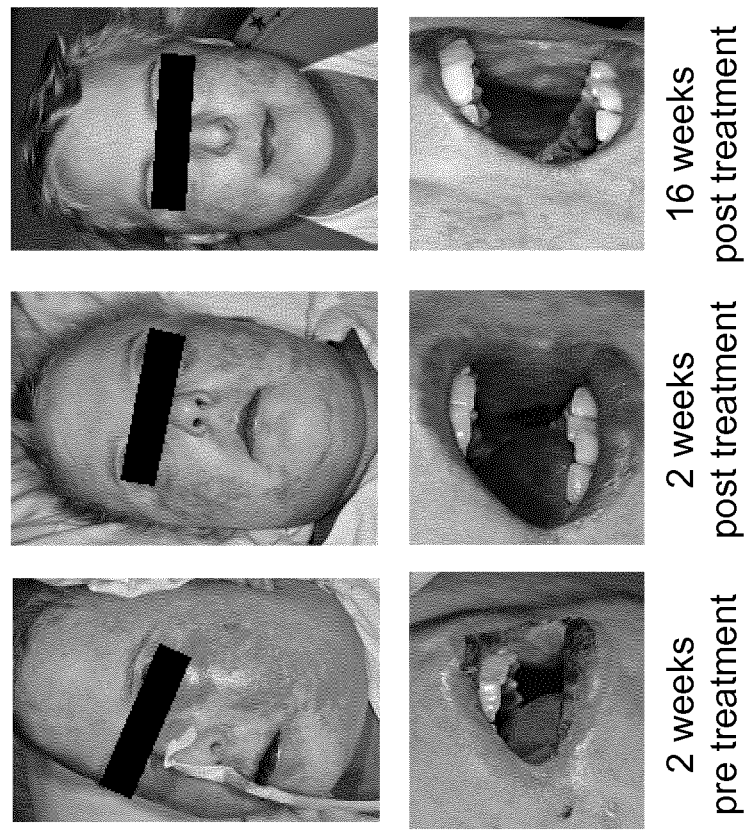

FIG. 4 also shows the transplantation-relevant effects of exosomes on a patient in a treatment scheme according to the examples. As symptom of the GvHD, the patient developed inflammations of the skin. After administration of MSC-derived exosome-enriched fractions, the symptoms were drastically reduced, without that other side-effects could be observed.

Figure 5:
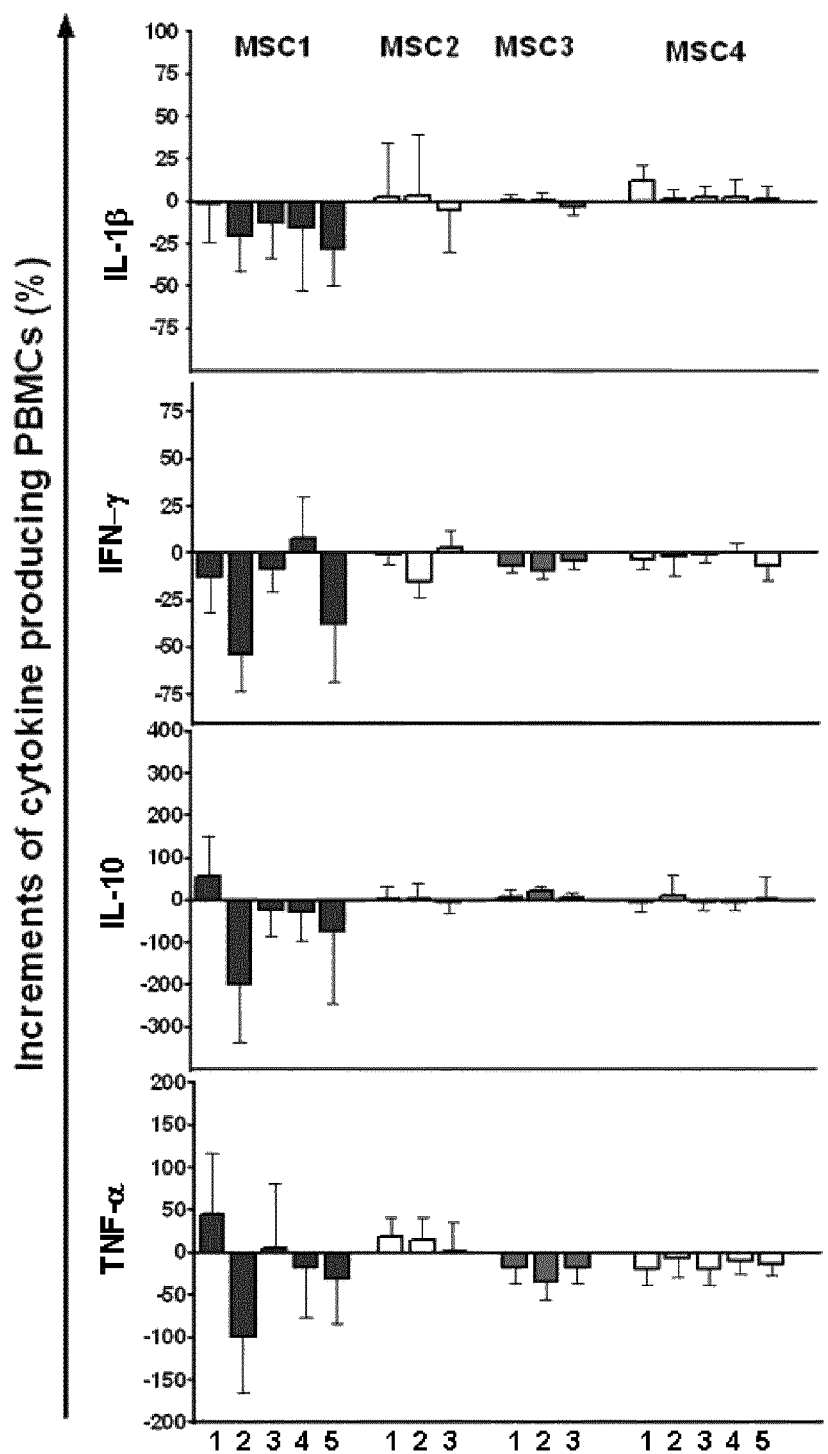

FIG. 5 shows that MSC-fractions, such as MSC1 Exo reduce the number of IL-1β, TNF-α and IFN-γ secreting PBMCs in almost all settings, in particular in vitro. Immune suppressive effects on the cytokine responses of the other exosome preparations (MSC2 Exo, MSC3 Exo and MSC4 Exo) are slightly less prominent.

Figure 6:
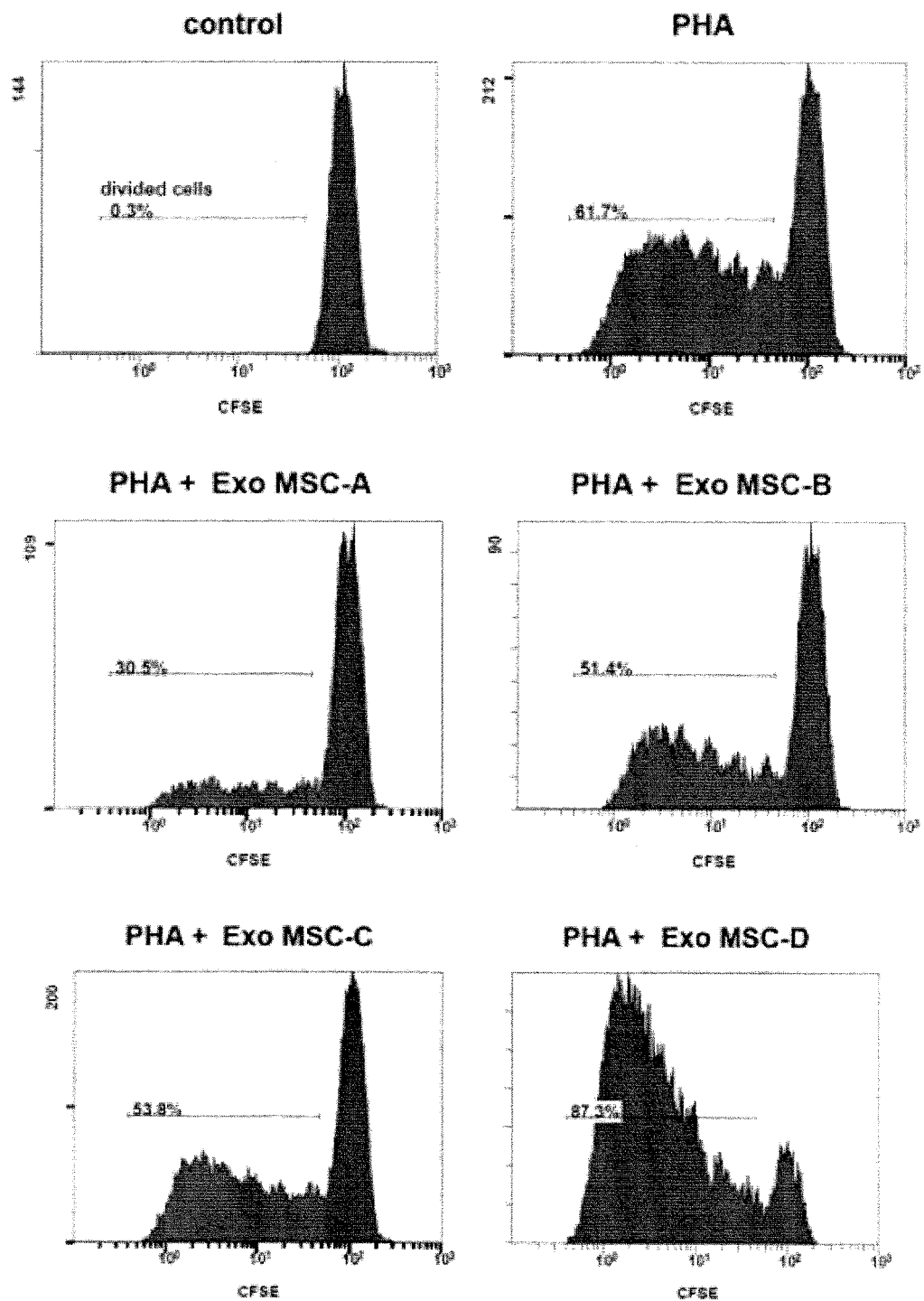

FIG. 6 shows that depending on the exosome fraction, MSC-enriched exosomes suppress, do not modulate or increase the proliferation rates of treated T cells, respectively (Example III).

Figure 7:
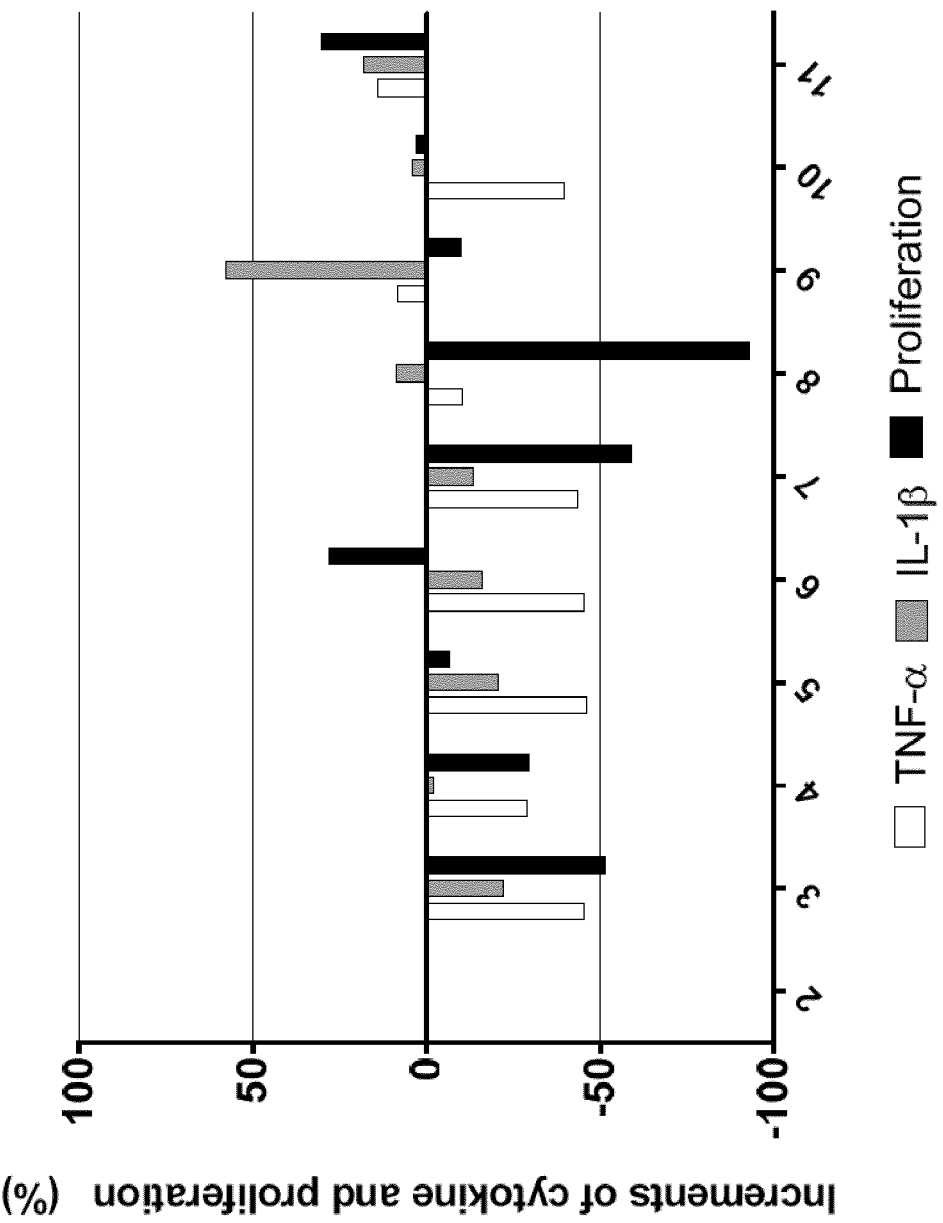

FIG. 7 shows that certain exosome fractions such as Exo MSC A (fraction 3 in FIG. 7) and MSC Exo F (fraction 7 in FIG. 7) suppress proliferation of PHA stimulated T cells and IL-1 beta and TNFalpha release of stimulated T cells (see Example III).

Figure 8:
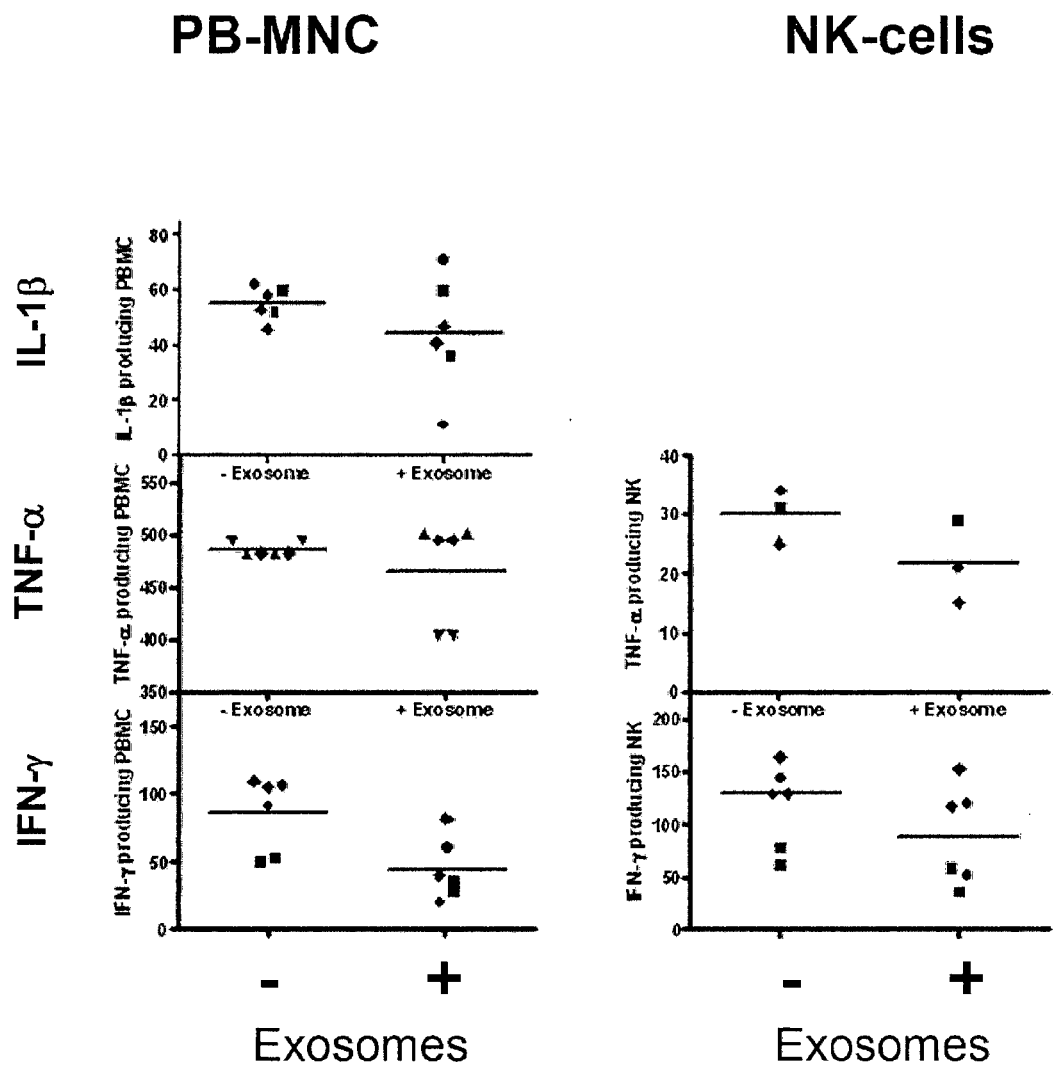
Figure 8:
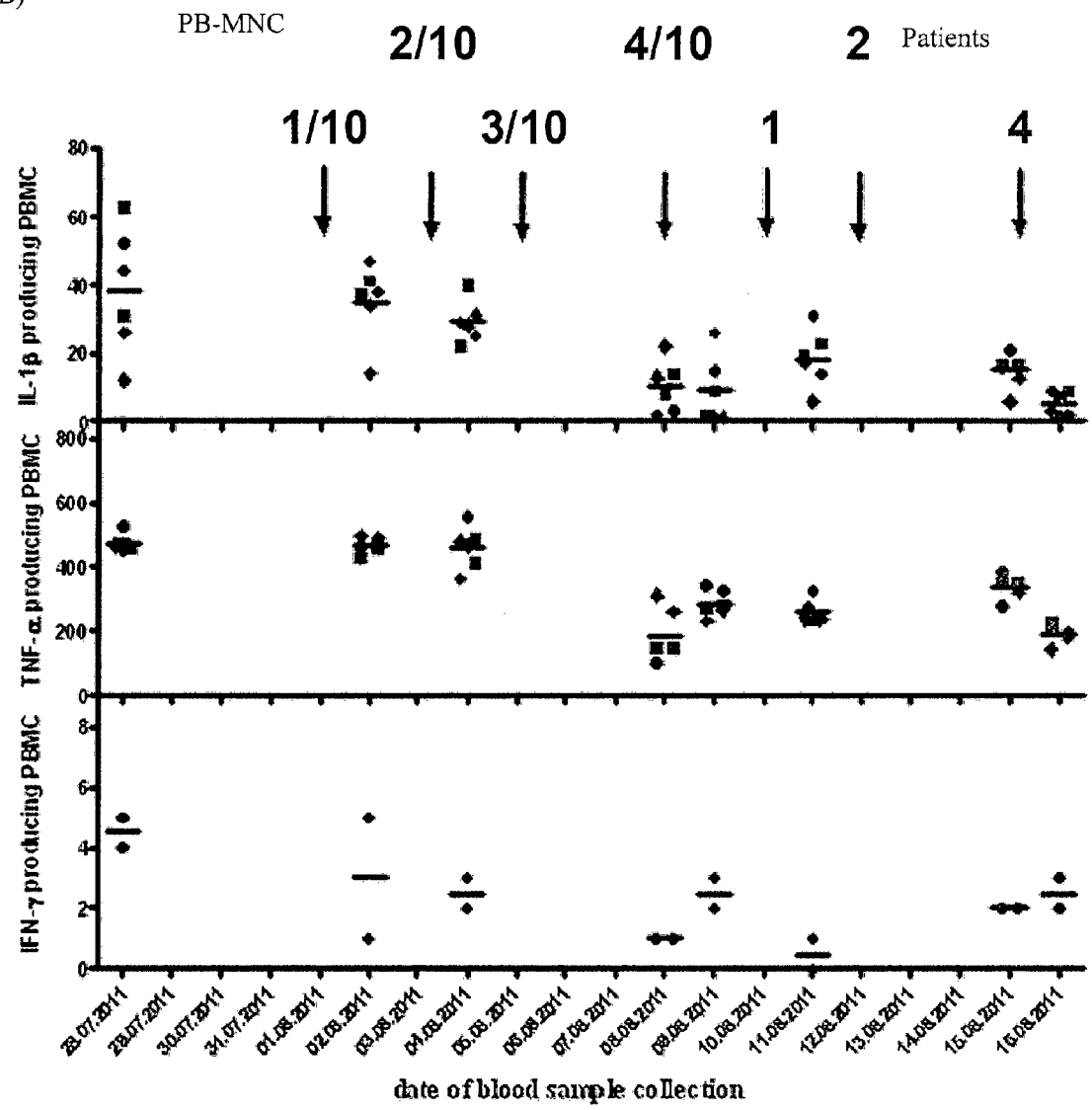

FIG. 8 shows that the effects of the in vitro studies (A) correlate with the effect in vivo (B).

EXAMPLES

Example I

Distinct MSC Exosome Preparations Contain Different Cytokine Compositions

The exosome-enriched fractions derived from the four MSC preparations were analyzed for their content of anti- and pro-inflammatory as well as apoptosis-inducing molecules (Table 1). Apart from the pro-inflammatory cytokines IFN-γ and IL-8, the exosome preparations contained high quantities of the anti-inflammatory molecules IL-10, TGF-β1 and HLA-G. Neither the pro-inflammatory cytokines IL-1β, IL-2, IL-6, IL-17a, IL-21 and TNF-α, the anti-inflammatory cytokines IL-1β Ra and IL13, nor the apoptosis-inducing molecule sFasL were detected in any of the exosome preparations (Table 1).

Especially the MSC1 exosome preparation (MSC1 Exo) contained elevated TGF-β levels, which surpassed TGF-β plasma levels of healthy donors by more than the factor 10. In addition MSC1 Exo differed from the others preparations with regard to the anti-inflammatory cytokine IL-10 and the pro-inflammatory cytokine IFN-γ. The ratio of IL-10 to IFN-γ varied between the four exosome preparations for almost two orders of magnitude (Table 1); the highest ratio was found for MSC1 Exo (1.02).

TABLE 1

Cytokine contents of the MSC exosome preparations.

| | Marker | MSC1[3] | MSC2 | MSC3 | MSC4 | control[4] |
|---|---|---|---|---|---|---|
| Pro-inflammatory | IL-1β[1] | 0 | 0 | 0 | 0 | 0-34 |
| | IL-2[1] | 0 | Not tested | Not tested | Not tested | 0-44 |
| | IL-6[1] | 0 | Not tested | Not tested | Not tested | 0-8 |
| | IL-8[1] | 48.2 | 11.4 | 7.8 | 15.7 | 0-31 |
| | IL-7a[1] | 0 | Not tested | Not tested | Not tested | Not tested |
| | IL-21[1] | 0 | Not tested | Not tested | Not tested | Not tested |
| | TNF-α[1] | 0 | 0 | 1.9 | 0 | 0-10.4 |
| | IFN-γ[1] | 81.5 | 38.2 | 83.5 | 144 | 0-56 |
| Anti-inflammatory | IL-1β Ra[1] | 0 | 0 | 0 | 0 | Not tested |
| | IL-4[1] | 0 | 15.2 | 14.9 | 69.1 | 0-5 |
| | IL-10[1] | 83.3 | 0.98 | 9.7 | 42 | 0-625 |
| | IL-13[1] | 0 | Not tested | Not tested | Not tested | Not tested |
| | TGF-β1[1] | 13516 | 305 | 135 | 579 | 903-1654 |
| | sFasL[1] | 0 | 0 | 0 | 0 | 90-2285 |
| | HLA-G[2] | 26.4 | 6.3 | 3.1 | 9.8 | 0-56 |
| ratio | IL-10:IFN-γ | 1.02 | 0.03 | 0.12 | 0.03 | |

[1]Levels are given in pg/mL;
[2]Levels are given in ng/mL;
[3]Preparation used for treatment;
[4]N = 20 for healthy controls Distinct MSC Exosome Preparations Reveal Different Capabilities to Suppress Inflammatory Responses In Vitro Immune modulatory impacts of the MSC exosome preparations were tested in a mixed lymphocyte reaction using the HLA class I negative K562 as target cells. In order to reflect an allogeneic transplantation setting stable HLA-B35, HLA-E*01:03 or HLA-B27-transfected K562 variants and cells of the HLA class I positive, respiratory syncytial virus infected (RSV) B-cell line were additionally used as allogeneic target cells. In three independent experiments target cells were co-cultured with PBMCs of healthy donors, either in the presence or absence of MSC exosomes. Numbers of IL-1β, TNF-α and IFN-γ secreting PBMCs were documented within the ELISpot assay as mean percentage±SEM.

Compared to the co-cultures without exosomes, MSC1 Exo reduced the number of IL-1β, TNF-α and IFN-γ secreting PBMCs in almost all settings (FIG. 5), in particular in vitro. Immune suppressive effects on the cytokine responses of the other exosome preparations (MSC2 Exo, MSC3 Exo and MSC4 Exo) were less prominent (FIG. 5). These findings suggest that depending on the expanded MSCs, MSC-derived exosomes exert different immune modulatory functions.

Immunomodulatory Effects of Exosomes In Vitro Propagation of MSCs

Primary human MSCs were raised from mononuclear cells obtained by Ficoll density gradient centrifugation of bone marrow and raised mainly as described before (Hemeda et al., 2010). Instead of 10% fetal bovine serum (FBS) the inventors supplement the basal media with 5% human pooled platelet lysates. To exclude variations caused by the usage of different platelet lysate preparations, the inventors performed all experiments with the same batch of platelet lysates that the inventors produce by pooling 3040 individual human platelet samples. Growth conditions in the presence of human platelet lysates instead of animal sera such as FBS comply with GMP standards and are applicable for clinical settings (Doucet et al., 2005; Schallmoser et al., 2007 & 2009; Lange et al., 2007). MSCs were characterized by flow cytometry as $CD90^+/CD73^+/CD105^+/CD44^+$ cells lacking the expression of CD45 and the endothelial marker CD31. MSC differentiation capability along the osteogenic, cartilage and adipogenic lineage was evaluated.

Collection of MSC Conditioned Media and Purification of Exosomes

Starting at passage 3 conditioned media (CM) were harvested every 48 h and passed through a 0.22 μm filter membrane to remove cell debris and larger vesicles. CM were collected and stored at −20° C. After thawing, CM were unified and processed by PEG precipitation. Briefly, PEG 6000 was added to CM. Following incubation for 8-12 h at 4° C. exosomes were precipitated by centrifugation for 30 min at 1500 g. Obtained pellets were resolved in 1 mL 0.9% NaCl, washed in a total volume of 45 mL 0.9% NaCl for 12 h at 4° C. and precipitated by ultracentrifugation for 2 h at 100,000 g. Again pellets were resolved in 1 mL of 0.9% NaCl, diluted with 0.9% NaCl to required concentrations and stored as 1 mL aliquots at −80° C. until use.

Quality Control of Exosomes

Protein concentrations of obtained aliquots were determined. Of each lot, 10 μg of exosome containing fraction was used to perform Western blots with antibodies recognizing exosome specific marker proteins, such as Tsg101, CD63, CD81 or CD82. Additionally, the inventors measured the concentration and size of the exosome by the NTA method as described previously (Sokolova et al., 2011). The concentration of pro- and anti-inflammatory cytokines (e.g., IL-1β, IL-6, IL-8; TNF-α, IFN-γ, IL-4, IL-10, IL-13, TGF-β1, TSG-6) and of the Fasligand within the exosome fractions were measured using the Luminex method. Other methods that could be used include, for example, ELIspot, ELISA, and/or flow cytometry.

Immunomodulatory Effects In Vitro

As an immunomodulatory read out, the inventors established the T-cell/MNC proliferation assay within the group. In analogy to the inventors' $CD34^+$ cell studies (Beckmann et al., 2007; Giebel et al., 2006) MNCs or magnetic cell separation enriched $CD3^+$ cells were stained either with CFSE or PKH2 and raised in the presence of either a T cell/MNC proliferation stimulating agents (e.g. LPS, PMA, PHA, anti-CD3 beads) or of cells of the leukemic cell line K562. First, the inventors established a protocol allowing them to document T-cell/MNC proliferation by flow cytometry. Next, the inventors searched for a stimulant whose impact on the T cells1MNCs could effectively be modulated by MSC exosomes. Finally, the inventors found a stimulant, which triggered proliferation of different leukocytes within MNC fractions. Using gating strategies for B, T and NK cells the inventors analyzed impacts of MSC exosomes on these cells separately. To estimate effects of MSC-derived exosomes on the cytokine secretion of B, T and NK cells the inventors used the ELISpot assay. Furthermore, the inventors adapted a flow cytometry based cytokine secretion assay (Miltenyi, Bergisch-Gladbach), allowing them to study the effect of MSC exosomes on the release of pro-inflammatory cytokines (specifically IFN-α, TNF-α and IFN-γ) by stimulated immune cells.

Comparison of Immunomodulatory Activities of Different MSC Exosome Preparations

Using the aforementioned assays the inventors compared the immunomodulatory activities of 15-20 independently obtained MSC exosome fractions. The inventors expected that some of these fractions would show strong immunomodulatory activity, whereas others would have no effect on the immune response of stimulated immune cells. The three samples with the highest and the lowest immunomodulatory activities were compared in more detail. The inventors also comprehensively compared the expression profiles of the MSC propagations, from which corresponding exosome fractions were obtained. The inventors identified sets of candidate proteins that predicted immunomodulatory effects. The inventors validated these markers by evaluating their expression in additional MSC and exosome samples.

Immunomodulatory and Neurorestorative Effects of Exosomes In Vivo

MSC-derived exosomes using PEG preparations with high and low immunomodulatory capabilities in vitro were used for the in vivo approach. C57bl6 mice were submitted to 30 minutes of intraluminal middle cerebral artery occlusion. This model is well characterized and has been extensively used in the inventors' lab before, resulting in localized infarcts of the striatum and most lateral cerebral cortex (Doeppner et al., 20096). Dissolved in a volume of 250 μL, $2 \times 10^6$ cell equivalents of exosomes were injected over 10 min via tail vein on days 1, 3, and 5 post-stroke. To compare effects of exosomes with those of MSCs, additional animals are examined, which received transplantations of MSCs used for the generation of exosome fractions. In these animals, a total of $1 \times 10^6$ MSCs dissolved in 250 μL normal saline were transplanted on day 1 post-stroke by intravenous injection. The latter animals receive normal saline injections on days 3 and 5. Vehicle-treated control animal were also prepared that receive injections of 250 μL normal saline only on days 1, 3 and 5 post-stroke. Four survival time points were examined, at which animals were sacrificed (7 d, 28 d, 56 d and 84 d after the stroke). Finally, four survival times were assessed in a total of 12 animals per condition and time point, resulting in a total of 240 animals, considering two exosome sources (immunomodulatory and nonimmunomodulatory) plus their corresponding MSCs.

Analysis of Post-Ischemic Motor and Coordination Deficits

Post-ischemic motor and coordination deficits were analyzed using the rota rod, the tight rope and the corner turn test as previously described (Zhang et al., 2002; Doeppner et al., 2011b). All animals were trained 1-2 days before induction of stroke to ensure sufficient test performance. Actual tests are performed on days 7, 14, 28, 56 and 84. Using the rota rod test, animals were put on a treadmill with an accelerating speed of 4-40 rpm. The maximum speed was achieved after 260 s, and maximum testing time was 300 s. The time until animals drop was registered and statistically analyzed. For the tight rope test, animals were placed on a 60 cm long rope grasping the string with their forepaws. Maximum test time was 60 s, and results were scored from 0 (minimum) to 20 (maximum) according to a validated score. For the corner turn test, two vertical boards were attached at one side with an angle of 30°, and each mouse was tested for the side chosen over 10 trials per test day. Whereas healthy animals left the corner without side preference, mice suffering from stroke preferentially turned to the left, non-impaired body side. Thereafter, the laterality index (LI) was calculated according to the following formula: (number of left turns−number of right turns)/10.

Analysis of Post-Ischemic Structural Brain Injury, Endogenous Neurogenesis, Axonal Plasticity and Angiogenesis Brain injury was analyzed at the time points given using cresyl violet staining, NeuN staining, TdT-mediated dUTP-biotin nick end labeling (TUNEL) staining and analysis of astroglial scar formation using the astrocytic marker glial fibrillary acidic protein (GFAP). Since transplantation of stem cells can support endogenous repair mechanisms, postischemic neuroregeneration after exosome treatment was analyzed as well. Therefore, mice received daily intraperitoneal injections of bromodeoxyuridine (BrdU) on days 8-18, to indirectly assess post-ischemic cell proliferation. After sacrifice of animals at the time points given, immunohistochemial double staining against BrdU and various "differentiation" markers (e.g., Dcx, NeuN, CNPase) were performed (Doeppner et al., 2010b). To evaluate axonal plasticity, animals also received ipsi- and contralateral injections of the anterograde tract tracer biotinylated dextran amine (BDA) and cascade blue labeled dextran amine into the motor cortex on day 70 in order to determine exosome-induced pyramidal tract sprouting on day 84 post-stroke (Reitmeir et al., 2011). For analysis of angiogenesis, immunohistochemical protocols using the marker CD31 were employed (Wang et al., 2005). Tissue samples were collected for studies other than immunohistochemistry, such as realtime PCR, which allowed to evaluate post-ischemic inflammation, neuronal viability and astroglial scar formation. These assays included real-time PCR protocols according to the manufacturers' protocols.

Analysis of Post-Ischemic Cerebral Immune Cell Infiltration and Peripheral Immune Response In order to assess quantitative changes of cerebral immune cell infiltration, FACS analysis was performed on day 7 post-stroke. In line with published protocols (Gelderblom et al., 2009), the inventors analyzed the relative frequency of microglia, neutrophils, macrophages, dendritic cells, natural killer cells and lymphocytes in brain tissue. Since stem cell induced neuroprotection also implies modulation of peripheral immune responses (Schwarting et al., 2008), peripheral immune cell subtypes were analyzed in the spleen, lymph nodes and blood. More specifically, a differentiation analysis of CD11b$^+$ and CD11c$^+$ antigen-presenting cells and of lymphocyte subpopulations was performed.

Example II

As an undesired side effect of allogeneic bone marrow transplantation, some patients with malignant hematological diseases develop GvHD, i.e. a condition, in which the new immune system recognizes the patient's tissue as 'foreign' and attacks it. Usually, transplanted patients receive immunosuppressant treatments. Patients refractory to such treatments have a poor prognosis, while transplanted MSCs might improve the clinical response (Gotherstrom et al., 2004; Le Blanc et al., 2004). Meanwhile it is assumed that the immunomodulatory activities of MSCs result from secreted soluble factors rather than direct cellular interactions between engrafted MSCs and the patient's immune cells (Baron and Storb, 2012). The inventors hypothesized that the effectors are MSC-derived exosomes.

Given the history of a female patient with myelodysplastic syndrome that had received allogeneic bone marrow transplantation, the patient developed a refractory, severe GvHD. After written consent and approval by local ethics authorities, the inventors transfused MSC-derived exosomes for the very first time ever in man for compassionate use ('individueller Heilversuch'). Before delivery, the inventors purified exosomes from four different MSC lineages and tested their immunomodulatory properties extensively in vitro.

The inventors observed immunosuppressive properties of these exosomes in 3 out of 4 lineages. Next, the inventors chose exosomes with the strongest immunomodulatory effect, tested their interaction with the patient's blood cells in vitro and transfused the exosomes in intervals of 2-3 days in increasing doses into the patient (FIG. 3). The patient tolerated the exosome application very well and remarkably recovered from her GvHD symptoms during and after the therapy (FIG. 3). The patient was stable for more than 5 months. Even though the inventors cannot conclude at this state that the MSC exosomes led to the suppression of the GvHD symptoms, the patient's immune cells surprisingly showed a similar immune modulation as cells of healthy donors cells which were treated with exosomes in vitro.

Isolation of Primary Human Mesenchymal Stem Cells

Human bone marrows (BM) were obtained from unrelated donors after informed consent according to the Declaration of Helsinki. Primary human MSCs were generated from mononuclear cells obtained by Ficoll (Biocoll Separating Solution, Biochrom AG, Berlin, Germany) density gradient centrifugation of bone marrow. The mononuclear cells were cultured in tissue culture 6 well plates at a density of 2×10$^6$ cells per well in MSC basal media (PAN) supplemented with 5% thrombocyte lysate, 1% glutamine, and 1% penicillin-streptomycin (PAA) for 24 hours. After 24 hours of incubation non-adherent cells were removed by medium exchange. After confluence had been reached, usually within 14 days, cells were continuously passaged after treatment with 0.25% trypsin. Adherent cells showed fibroblast-like morphology, and were able to differentiate along the adipogenic, chondrogenic, and osteogenic pathways.

Exosome Isolation and Purification (First Variant)

Exosomes were isolated from cell culture supernatants of MSCs derived from bone marrow. To remove cells, conditioned media were centrifuged for 5 min at 900×g, and to remove remaining debris, another centrifugation step was performed for 1 h at 10,000×g. To remove all particles bigger than 200 nm, the supernatants were filtered through 0.2 um pore filters. To concentrate the exosomes, the filtrate was centrifuged for 2 h, 110,000×g, at 4° C. The obtained precipitates were resuspended in 150 µl PBS and used for further analyses.

Exosome Isolation and Purification (Second Preferred Variant)

PEG-Precipitation of Exosomes from Conditioned Media of Adult Tissue, in Particular Adipose Tissue, Bone Marrow, Placental Tissue or Umbilical Cord Derived MSCs Starting at passage three, the inventors performed media exchanges every other day. MSC supernatants were collected and stored at −20° C. After thawing, the supernatants were unified and 3 units/mL of heparin and approx. 3 µg/mL Actilyse™ (Boehringer Ingelheim, Germany) were added. Supernatants were incubated for 3 h at 37° C., and then filtered through 0.22 µm bottle top filters.

Subsequently, a fraction of the medium (300 ml) was concentrated in 300 MWCO filters (Sartorius), the supernatant was precipitated either using 10% or 12% PEG 6000 or 10% PEG8000. For the precipitation, supernatants were transferred into 50 ml reaction vials (sterile, Greiner, Germany) prefilled with the precipitation reagent (PEG+NaCl). After mixing the vials were incubated over night (8-12 h at 4° C.).

On the next day, vials were centrifuged at 1500 g for 30 min at 4° C. The supernatants were carefully removed (25 ml pipette). To collect remaining supernatants, vials were centrifuged for another 5 min at 1500 g. Residual supernatant was removed using a 1 ml pipette. Pellets were resuspended in 1 ml NaCl 0.9%. To remove remaining PEG, resuspended precipitates were supplemented with 0.9% NaCl to a total volume of 45 ml and stored at 4° C. for about 12 h.

The 45 ml suspensions were split and transferred in half into two ultracentrifugation-vials. 0.9% NaCl was added to a total volume of 38 ml. The preparations were centrifuged for 2 h at 110.000 g. The supernatants were removed from the sediments as obtained; the supernatants were resuspended in 1 ml 0.9% NaCl solution, and pooled. Then, the sample was filled up to 10 ml using 0.9% NaCl solution, and frozen in 1 ml aliquots in 15 ml reaction vials at −80° C.

Exosome Isolation and Purification Via Monolithic Columns

The columns were used according to the instructions of the manufacturer (www.biaseparations.com), with adjustments where necessary.

The supernatants were also kept, and stored frozen at −20° C. Then, the aliquots were diluted 1:5 (0.9% NaCl solution), and used in the following assays:

Microbiological test, virulence test, protein content, activity test, pyrogen test, and particle size.

Protein Content

The protein contents were determined by the micro BCA assay (Thermo Fisher Scientific).

Exosome Specific Proteins

Exosome specific proteins were identified by Western blot analysis. For this, purified exosomes were treated with sample buffer (DTT, 0.1% SDS, 0.1 M Tris HCl, pH 7.0) and spoiled for 5 min at 95° C. Proteins were separated on 12% SDS-PAGE gel and transferred to PVDF membranes. Membranes were blotted with antibodies to Tsg101 (Sigma Aldrich), Flotilin 1 (BD Pharmingen), and CD81 (BD Pharmingen), then incubated with appropriate HRP-conjugated secondary antibodies (Dianova) and visualized by enhanced chemiluminescence (Pierce).

Nano Particle Tracking Analysis (NTA)

For particle size determination, NTA was performed with a NanoSight LM10 instrument equipped with the NTA 2.0 analytical software. All experiments were carried out at 1:2000 dilutions, resulting in particle concentrations of approx. $3 \times 10^8$ per mL. Each experiment was carried out in triplicate. The 50% median value (D50) is given in all cases, and the standard deviation was calculated for all data.

Peripheral Blood Samples

In order to monitor the cytokine reactivity profiles of peripheral blood mononuclear cells (PBMC), EDTA plasma samples were procured from donors as well as from the respective patient before, during and after the MSC-exosome therapy. PBMC were isolated from blood samples by Lymphoprep (Invitrogen, Karlsruhe, Germany) density gradient centrifugation and cryopreserved until further analysis.

Cytokine and HLA-G Determinations

Levels of soluble HLA-G (sHLA-G), cytokines and apoptosis-inducing molecules in MSC-exosome preparations were analyzed by ELISA. Before performing the various ELISA formats, exosomes (approx. $60.5 \times 10^8$ particles) were solubilized in 1 ml PBS-Tween (1%) and sonicated for 60 sec. sHLA-G concentrations were determined as described before (Schutt et al., 2010) with minor modifications: The monoclonal antibody (mAb) G233 (Exbio, Praha, Czech Republic) was used as capture reagent and bound sHLA-G was detected by the biotinylated mAb w6/32 (Leinco Technologies, St. Louis, Mo., USA) followed by AMDEX™ Streptavidin HRP (Amersham, Freiburg, Germany). The detection limit of sHLA-G ELISA was 0.1 ng/ml. Concentrations of pro-inflammatory (IFN-γ, TNF-α, IL-1b, IL-2, IL-6, IL-8, IL-17a, IL-21), anti-inflammatory (IL-1βRA, IL-4, IL-10, IL-13, TGF-β1) and apoptosis-inducing molecules (soluble FasL) were determined according to the manufacturers' protocols (eBioscience, Frankfurt, Germany or BD Biosciences, San Jose, Calif., USA). The assay sensitivities ranged between 2.0 and 20 pg per mL.

Determination of the IL-1β, TNF-α, and IFN-γ Cytokine Reactivity Profile by ELISpot After thawing, PBMC and NK cells, isolated by negative selection out of these PBMC (Invitrogen, Karlsruhe, Germany), were adjusted to a fixed concentration of $1 \times 10^6$ cells/mL and used as effector cells. To analyze the influence of the MSC-exosomes on the cytokine response $1 \times 10^6$ effector cells were mixed with approx. $60.5 \times 10^8$ MSC-exosomes. In this case effector cell suspensions with exosomes and without exosomes were used in cytokine stimulation experiments. HLA-E*01:03, HLA-B35 or B27 transfected K562 cells and the parental HLA class I neg. K562 cell line served as stimulator cells and were adjusted to a concentration of $0.1 \times 10^6$ cells/mL. All ELISpot assays were performed in an effector/stimulator ratio of 6:1. For the IL-1β and the TNF-α ELISpot assays, $12.5 \times 10^4$ effector cells and $0.25 \times 10^4$ stimulator cells and for the IFN-γ ELISpot assay, $75 \times 10^4$ effector cells and $1.5 \times 10^4$ stimulator cells were seeded with 200 µl culture medium containing 200 U/mL IL-2 and 10% fetal calf serum onto MultiScreen-HA ELISpot plates (MAIPS4510, Millipore, Bedford, Mass., USA) pre-coated with the respective capture antibody of the ELISpot Kit (eBioscience, Frankfurt, Germany). Effector cells without stimulator cells and stimulator cells without effector cells served as controls. Each stimulation condition was performed in duplicate. After 24 h incubation at 37° C. under 5% $CO_2$ numbers of cytokine producing effector cells were detected according to manufacturer's protocol. Spots were enumerated by the ELISpot reader AID EliSpot Reader Systems (Autoimmun Diagnostika GmbH, Strassberg, Germany) using AID EliSpot Software Version 6.x.

Characteristics of Exosomes that were Prepared from Propagated MSCs of Four Different Donors Cell numbers, amount of harvested culture media, number of obtained exosomes and features of the obtained exosome fractions (particle numbers, protein amount etc.)

Protein content of the sample: 1.1 mg/ml;

Particle size: 199.5+/−70 nm;

Particle number: $6.02 \times 10^{12}$ Particle/ml

Endotoxin content: 0.588 I.E./ml (+/−50%) corresponding to 2.94 I.E./ml of the concentrated solution.

Detection of Flotillin-1 and Tsg101 as exosome markers was confirmed using antibodies and Western blot.

MSC Preparation Exosomes Exerted Donor-Dependent Immunosuppressive Effects In Vitro Exosomes derived from four different MSC preparations were analyzed for the content of anti-, pro-, and apoptosis-inducing molecules: Besides the two pro-inflammatory cytokines IFN-γ and IL-8, MSC-exosomes contained preferentially high quantities of the anti-inflammatory and/or immune suppressive molecules IL-10, TGF-β1 and HLA-G. Especially, TGF-β1 levels were found to be ten times higher in the MSC-exosome solution of $60.5 \times 10^8$ particles/mL than in plasma levels of healthy controls.

Impact of Exosomses on PB-MNCs

The influence of the MSC-exosomes on the cytokine response of PBMC or NK cells of PB donors on K562 leukemic cells was proven by IL-1β, TNF-α and IFN-γ

ELISpot using. The donors effector cells were co-cultured with HLA class I negative K562 or genetically engineered K562 cells expressing HLA-E*01:03 or HLA-B35. It was found that the IL-1β, TNF-α and IFN-γ cytokine responses of the donor's effector cells were reduced towards the different allogenic cells in the presence of MSC-exosomes compared to responses in the absence of MSC-exosomes.

This implies that the MSC-exosomes are able to impair in vitro the capability of PBMC to produce pro-inflammatory cytokines known to be operative in GvHD.

Therapies Using Exosome Preparations According to the Present Invention

Figure 1:
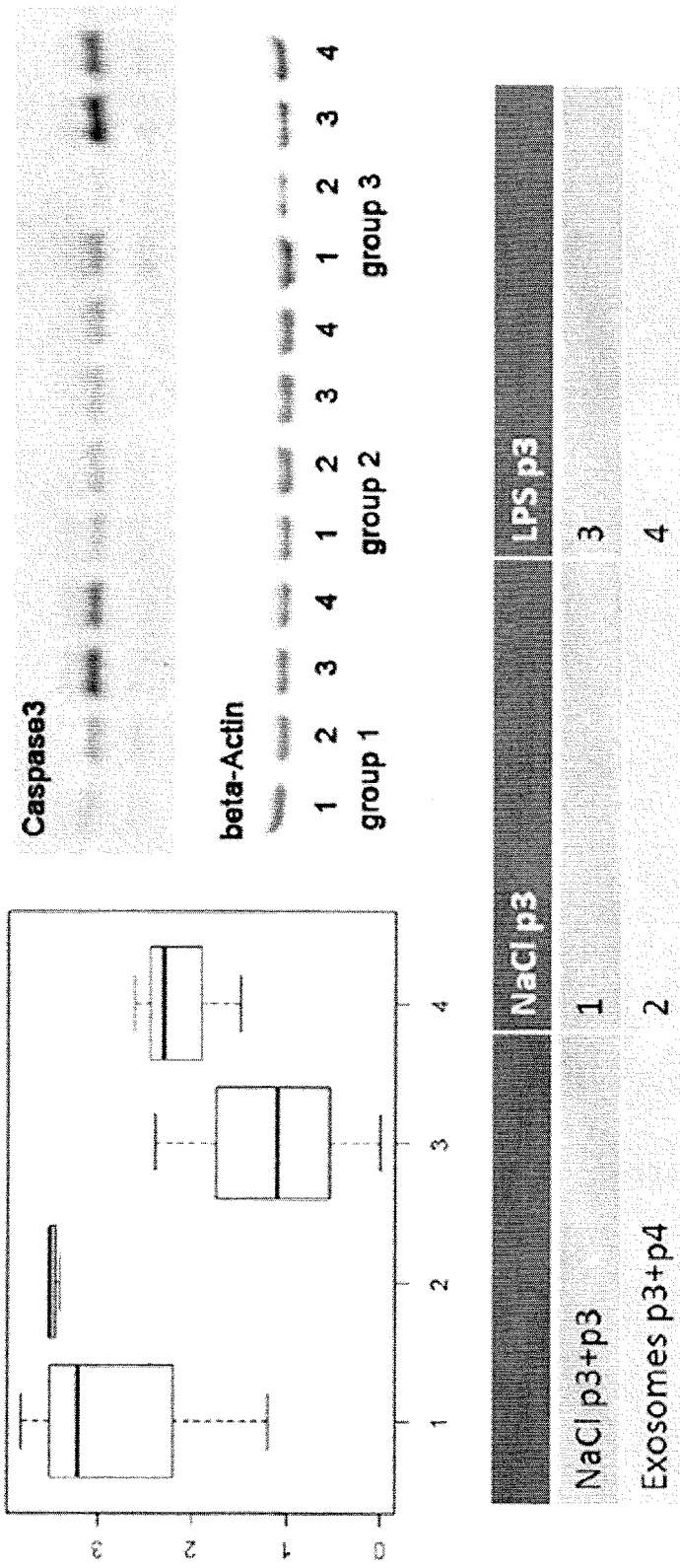
FIG. 1 shows the effect of exosome preparations on newborn rats that were partially confronted with LPS.
Figure 2:
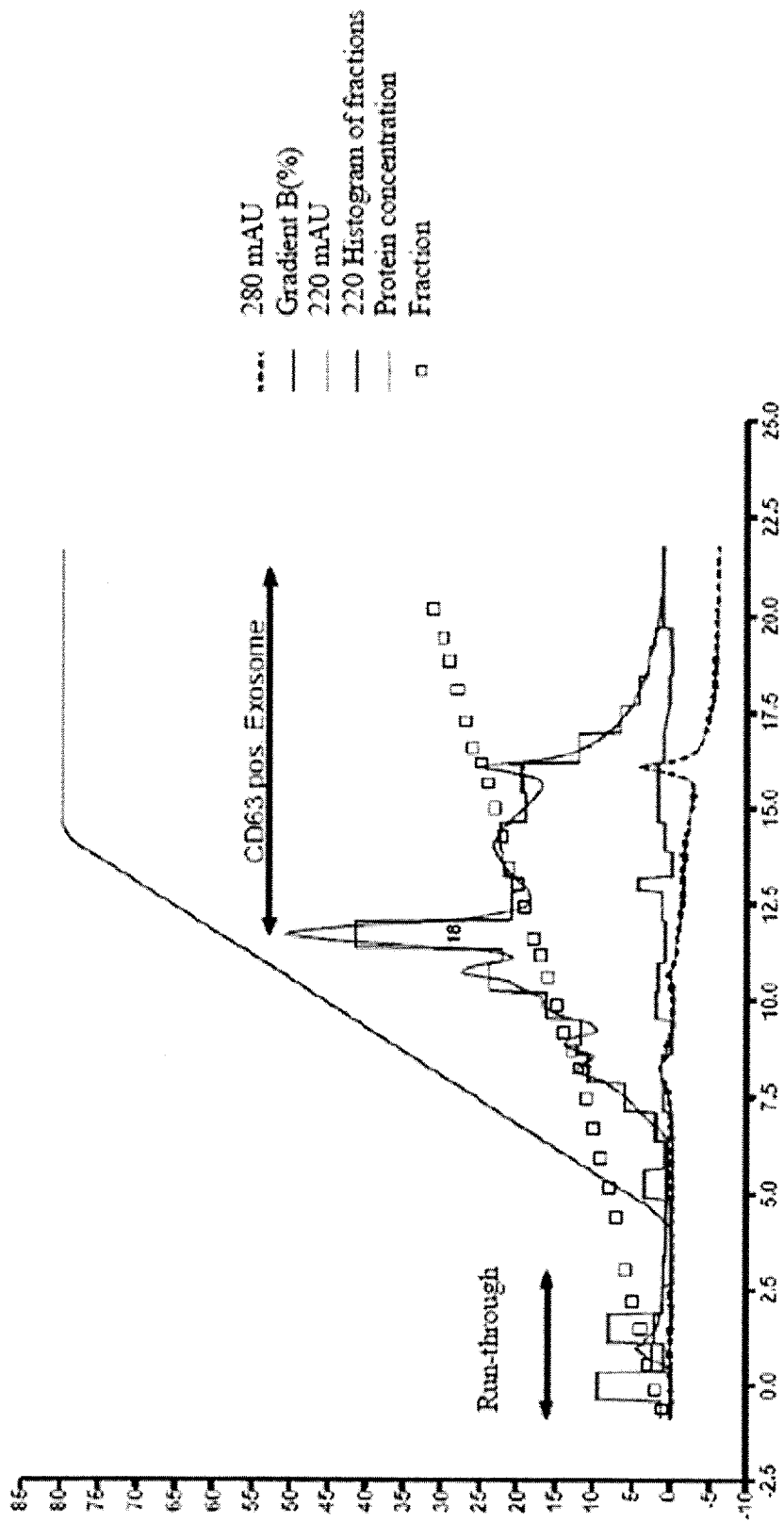
FIG. 2 shows an example for the analyses of exosomes-containing fractions during the purification thereof using a monolithic column.

Experiments in Rats (FIG. 1)

In order to show positive effects of the preparations of the invention, experiments with acquired damages of the brain in newborn rats were undertaken. After lipopolysaccharide (LPS) administration, treated animals do no longer show weight gain compared to control animals (A), furthermore, an increased expression of apoptosis markers is found in the brains of the treated animals (B). Both the loss of weight gain and the amount of the apoptosis marker (Caspase 3) as found is markedly reduced upon the simultaneous administration of MSC derived fractions that are enriched for exosomes (A, B).

Human Treatment (see FIGS. 3 and 4)

History of the patient—The 22-year old female patient received an allogeneic stem cell transplantation (AlloSCT) due to a myelodysplastic syndrome (MDS RAEB-T) with peripheral blood stem cells (PBSC) from a HLA-identical female donor following conditioning with busulfan, cyclophosphamide and melphalan.

After the first AlloSCT she developed mucosal GvHD but recovered hematologically with full donor chimerism. In October 2010 she suffered a relapse as a secondary acute myeloid leukemia (AML) with 57% blasts in the bone marrow examination. FLT3- and NPM-mutations were detectable. Therefore, in January 2011 a second AlloSCT with PBSC from a HLA-identical male donor following conditioning with hyper-fractionated total body irradiation with 12 Gy and cyclophosphamide was performed. GvHD prophylaxis was standard CSP and a short course of MTX. She suffered a hyperacute GvHD of the skin with general erythema and bullae, grade IV, which initially responded sufficiently to high-dose steroid-therapy. Thus, the patient could be discharged with a dual immunosuppression of CSP and steroids. Unfortunately, the GvHD worsened shortly after discharge and the patient had to be admitted to hospital again in March 2011 with exacerbated skin GvHD and now also severe GIT involvement. She had therapy-refractory nausea and vomiting, abdominal cramping and diarrhea volumes reached up to five liters/day. The intestinal GvHD was repeatedly documented be endoscopy and histological examination.

The severe GvHD did not respond to a number of immunosuppressive lines. The patient immediately upon re-admission received high-dose steroids (5 mg/kg body weight [BW]) with no obvious improvement. Therefore, a course of anti-thymocyte globulin (10 mg/kg BW) was applied over five days which also did not lead to a response. Then, mycophenolate mofetil (MMF) and subsequently tacrolimus were added and since in some colon biopsies HHV-6, adeno and EBV virus DNA was detectable, a therapy course with cidofovir was initiated in late April 2011, too. Unfortunately, all these measures did not lead to a relief in GvHD symptoms. Therefore a course of infliximab (10 mg/kg BW once per week over a four week period) was initiated and 17 sessions of extracorporeal photopheresis were performed over four months. Throughout this time the basic immunosuppression with steroids, mostly in combination with either tacrolimus or MMF, was continued.

Given the history of this refractory and severe GvHD and the continuous suffering of the patient an experimental approach to control the GvHD symptoms was pursued after intensive discussion. A concept for an individual treatment attempt with MSC-exosomes was developed and approved by the Ethical Committee of the University Hospital of Essen, Germany. The patient agreed to the proposed treatment and gave her written consent.

Exosome Application in Increasing Doses

The MSC-exosomes were administered between Aug. 1 to Aug. 15, 2011 in increasing doses.

| Application | Date | Dosage |
| --- | --- | --- |
| 1 | 2011 Aug. 1 | 1 ml of a 1:10 diluted exosome aliquot (100 µl) |
| 2 | 2011 Aug. 3 | 2 ml of a 1:10 diluted exosome aliquot (200 µl) |
| 3 | 2011 Aug. 5 | 3 ml of a 1:10 diluted exosome aliquot (300 µl) |
| 4 | 2011 Aug. 8 | 4 ml of a 1:10 diluted exosome aliquot (400 µl) |
| 5 | 2011 Aug. 10 | 1 ml of undiluted exosome aliquot |
| 6 | 2011 Aug. 12 | 2 ml of undiluted exosome aliquot |
| 7 | 2011 Aug. 15 | 4 ml of undiluted exosome aliquot |

The patient received pre-medication with steroids and anti-histamins prior to each MSC-exosome application and was closely monitored in the intensive care unit. The therapy was tolerated very well, and no side effects were detected. After each administration, blood samples were taken and analyzed for their capability to produce IL-1β, TNF-α, and IFN-γ in response towards K562, and K562 transfected with HLA-E*01:03 or HLA-B27 (see above).

After the third MSC-exosome application the PBMC of the patient started to lessen their cytokine reaction towards the stimulator cells. Compared to the cytokines' responses before MSC-exosome therapy the numbers of IL-1β, TNF-α and IFN-γ producing PBMC were found to be reduced more than fifty percent after the last application (p<0.0001, One-way ANOVA). Thus, it seems that the MSC-exosomes are able to impair in-vivo the capability of PBMC to produce pro-inflammatory cytokines known to be operative in GvHD.

GvHD in the Patient During and Following Exosome Treatment

In line with the reduced cytokine reaction profile during the course of MSC-exosome therapy the clinical GvHD had improved significantly shortly after the beginning of treatment: The skin manifestation clearly lost activity, nausea, vomiting and diarrhea were dramatically reduced. The cutaneous and mucosal GvHD showed a remarkable response within two weeks which was stable even after 16 weeks after exosome therapy. The diarrhea volume, too, was objectively reduced after exosome therapy. Due to the response, the dosage of the immunosuppressive agents could be reduced.

Example III

Comparison of Immune Modulatory Activities of Exosome-Enriched Fractions Obtained from Different MSC Preparations The inventors compared the immune-modulative activity of exosome-enriched fractions obtained from 10 independent MSC preparations within T cell assays. To measure the exosomes' impact on the proliferation of phytohemagglutinin (PHA) stimulated T cells, exosomes equivalents of 800.000 MSCs (corresponds to 0.02 Units of the exosome enriched fractions) were added into each reaction. Apart of the control, approx. 200.000 CFSE stained, living PB-MNCs of given donors were stimulated with the lectin PHA (final concentration: 200 ng/ml) for 5 days. Thereafter, cells were stained with anti-CD3 antibodies and analyzed by flow cytometry in two independent experiments. As highlighted in FIG. 6, all nonstimulated T cells retained their CFSE label. In contrast, a large proportion of PHA stimulated T cells showed reduced CFSE intensities indicating that these cells had been activated to divide.

Depending on the exosome fraction, MSC-enriched exosomes suppressed, did not modulate, or increased the proliferation rates of treated T cells, respectively (results of a characteristic experiment is given in FIG. 6; increments of all experiments are given as black bars in FIG. 7). These results demonstrate that exosome-enriched fractions obtained from independent MSC preparations differ in their ability to modulate the proliferative activity of PHA stimulated T cells.

In a second approach, PB-MNCs of 10 different peripheral blood donors were pooled. Aliquots of 400.000 cells were cultured in triplicates each in a total volume of 200 µl, either in the presence or absence of 0.02 U of the same exosome fractions presented in FIG. 6.

The release of the pro-inflammatory cytokines IL-1beta and TNF-alpha were documented by ELISA after 3 days. Increments of the release (%) in comparison to cultures without exosomes are documented in FIG. 7. Comparing the three parameters it becomes evident that certain exosome fractions such as Exo MSC A (fraction 3 in FIG. 7) and MSC Exo F (fraction 7 in FIG. 7) suppress proliferation of PHA stimulated T cells and IL-1beta and TNFalpha release of stimulated T cells. In contrast MSC ExoI promote proliferation of PHA stimulated T cells and forces and IL-1beta and TNFalpha release within the mixed lymphocyte reaction assay.

Thus, these results demonstrate that exosome enriched-fractions of different MSCs exert different immune modulatory functions.

LITERATURE AS CITED

Baron F, Storb R. Mesenchymal stromal cells: a new tool against graft-versus-host disease? Biol Blood Marrow Transplant. 2012 June; 18(6):822-40.

Lai, R. C., Arslan, F., Lee, M. M., Sze, N. S., Choo, A., Chen, T. S., Salto-Tellez, M., Timmers, L., Lee, C. N., El Oakley, R. M., et al. (2010). Exosome secreted by MSC reduces myocardial ischemia/reperfusion injury. Stem Cell Res 4, 214-222.

Lee, R. H., Pulin, A. A., Seo, M. J., Kota, D. J., Ylostalo, J., Larson, B. L., Semprun-Prieto, L., Delafontaine, P., and Prockop, D. J. (2009). Intravenous hMSCs improve myocardial infarction in mice because cells embolized in lung are activated to secrete the anti-inflammatory protein TSG-6. Cell Stem Cell 5, 54-63.

Schutt, P., Schutt, B., Switala, M., Bauer, S., Stamatis, G., Opalka, B., Eberhardt, W., Schuler, M., Horn, P. A., and Rebmann, V. (2010). Prognostic relevance of soluble human leukocyte antigen-G and total human leukocyte antigen class I molecules in lung cancer patients. Hum Immunol 71, 489-495.

The invention claimed is:

1. A method for producing a pharmaceutical preparation comprising exosomes that exhibit an immunomodulatory effect, wherein said immunomodulatory effect is selected from a reduced IL-1β, a reduced TNF-α and a reduced IFN-γ cytokine response of effectors peripheral blood mononuclear cells (PBMC) of a recipient of said preparation, said method comprising the following steps:
  a) providing a cell culture medium supernatant from neonatal or adult tissue-derived mesenchymal stem-cells (MSCs) that have been cultured in a medium supplemented platelet lysate, the cell culture supernatant comprising exosomes,
  b) enriching said exosomes via a method selected from at least one of differential centrifugation, filtration, polyethylene glycol precipitation and/or monolithic chromatography,
  c) quantifying said exosomes and analyzing at least one of the specific markers selected from CD63, CD81 and tumor susceptibility gene 101 (Tsg101), in said enriched exosomes,
  (d) determining an in vitro anti-inflammatory effect and/or an immune suppressive effect of said enriched exosomes by detecting at least one marker selected from anti-inflammatory molecules IL-10, TGF-β1 and HLA-G in said enriched exosomes,
  (e) determining a reduced IL-1β, a reduced TNF-α and/or a reduced IFN-γ cytokine response of donor effector PBMC cells incubated with said enriched exosomes,
  f) selecting those enriched exosomes that exhibit said anti-inflammatory effect and/or immune suppressive effect, wherein the levels of TGF-β1 as measured in an activity test are at least ten times higher than in plasma levels of healthy controls and wherein the ratio of IL-10 to IFN-γ is more than 1.

2. The method according to claim 1, wherein said preparation as produced is suitable for intravenous administration.

* * * * *

UNITED STATES PATENT AND TRADEMARK OFFICE
CERTIFICATE OF CORRECTION

PATENT NO. : 9,877,989 B2
APPLICATION NO. : 14/414843
DATED : January 30, 2018
INVENTOR(S) : Dietrich Wilhelm Beelen et al.

Page 1 of 1

It is certified that error appears in the above-identified patent and that said Letters Patent is hereby corrected as shown below:

In the Specification

Column 1,
Line 44, "multi-lineage" should read -- multilineage --.

Column 9,
Line 46, "IL-1 beta" should read -- IL-1beta --.

Column 10,
Line 25, "IL-10$^{(1)}$...83.3...0.98...9.7...42...0-625" should read
-- IL-10$^{(1)}$...83.3...0.98...9.7...4.2...0-625 --.

Column 15,
Line 23, "Microbiological test," should read -- - Microbiological test, --.

In the Claims

Column 20,
Line 26, "supplemented platelet lysate," should read -- supplemented with platelet lysate, --.

Signed and Sealed this
Twenty-first Day of August, 2018

Andrei Iancu
*Director of the United States Patent and Trademark Office*